May 24, 1932.
W. R. ELDER
Plant Pat. 17
FREESIA
Filed June 17, 1931
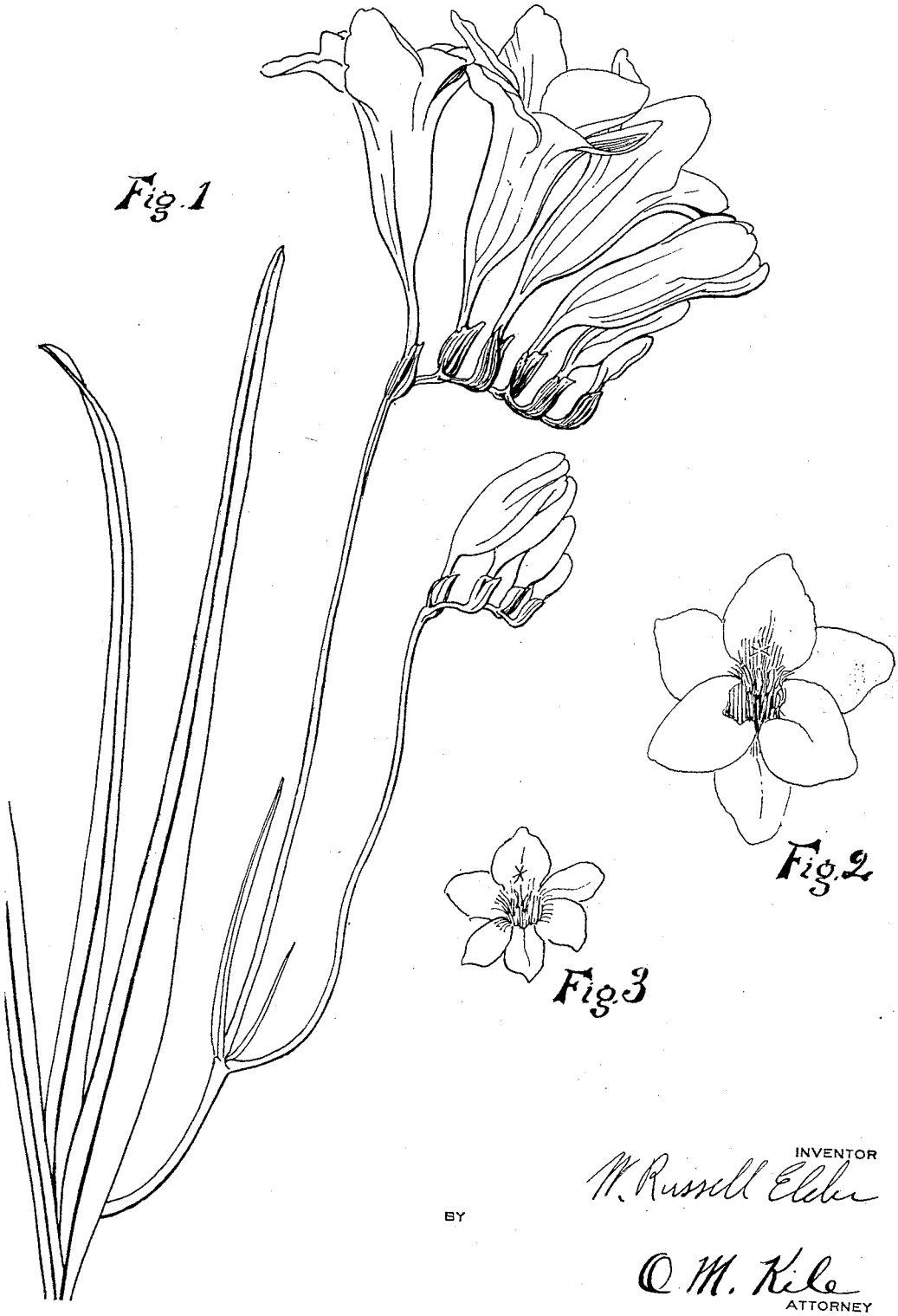
INVENTOR
W. Russell Elder
BY
O. M. Kile
ATTORNEY Patented May 24, 1932

Plant Pat. 17

UNITED STATES PATENT OFFICE

WILLIAM RUSSELL ELDER, OF INDIANAPOLIS, INDIANA, ASSIGNOR TO ELDER AND ELDER NURSERIES, OF INDIANAPOLIS, INDIANA, A CORPORATION

FREESIA

Application filed June 17, 1931. Serial No. 545,130.

My invention relates to improvements in fragrant white freesias. The object of my invention is to provide a freesia of the general type mentioned, having a much larger size both of plant and of blossoms, having flowers of more regular and pleasing form, having petals which appear pure, waxy white to the casual observer, having a brighter green foliage with long stems and upright growth, having exceptional reproduction and lasting qualities, and having other features which make it particularly suitable for florists' cut flower use.

This new freesia is a mutation which first appeared several years ago in a planting of mixed freesia seedlings in the commercial greenhouses of Elder Brothers at Indianapolis, Indiana. The parents of these seedlings were themselves seedlings from seed of several popular varieties of freesias. Some hand pollination had been done but pollination by bees had also taken place, therefore the exact parentage is obscure. The corms of this giant white freesia were carefully saved and a stock developed.

The variety was awarded a gold medal when first exhibited as a new variety and novelty at the National Flower and Garden Show of the Society of American Florists and Ornamental Horticulturists, in Louisville, Kentucky, in 1928. This variety was not introduced and sold to the public until the fall of 1930.

The accompanying drawings show in approximately natural size, (Fig. 1) a branch of my freesia, including several leaves, and two flower groups, (Fig. 2) a full front view of a single blossom, and (Fig. 3), for size comparison, a similar view of a blossom of the ordinary commercial variety heretofore known.

The following is a detail description of this new freesia:

Flowers: 5 to 6 flowers are borne upright and attached along a jointed axis which is suddenly bent back at right angles to the vertical peduncle. The perianth is tubular or funnel shaped, particularly long, slender and free from unsightly bulges; there is a marked freedom from irregularity in the length of the six segments of the perianth as compared with other varieties. The lobes are delicately rounded rather than pointed. Stamens are three in number, arising from the sides of the lower part of the tube; anthers, linear; ovary, ovoid, 3-celled; style, filiform and five-branched.

Color appearance is pure, waxy white except for the yellowish tube from point where stamens attach, on down to the ovary. While the appearance of the petals is lily-white and the yellowish lip found in most varieties is absent, close inspection of some of the blossoms, on the shortest lobe and in a location entirely obscured by overlapping lobes, discloses a yellow tinge. This yellow color is so hidden, however, as not to interfere with the lily-white appearance to the eye.

Sepals are two in number, broad, one-half inch long, one having a single deep division forming a two-toothed effect, completely covering the ovary.

Odor resembles that of orange blossoms and is more subdued than in most varieties of freesia.

Buds acquire a whitish color when one-fourth to one-half developed, and become almost fully white when two-thirds developed, thus giving a pleasing effect and not detracting from the white effect desired in a mass of cut freesias for bouquet purposes. Two to four flower group stems branch out from each main stem and bear buds, each group in an earlier state of development than the group immediately above and overhanging it.

The average diameter of the flowers of this giant freesia is about two to two-and-one-quarter inches, although single specimens grown under the usual cultural conditions have measured more than two-and-one-half inches in diameter.

The plants under average conditions grow 30 to 36 inches high and the leaves which are long and slender in appearance are about one-half inch wide at their widest points. The growth is sturdier and the leaves a brighter green than in other varieties of freesias. The stem or peduncle supporting the flower group is ordinarily about 10 inches long above the last leaf branch, slender but stiff and able to support the flower groups easily and without artificial aid.

Corms: The corms average much smaller in size than those of most other varieties, being ordinarily about ¼ to ¾ inch in diameter. Reproduction of this variety is several times as rapid as in most other varieties under similar conditions, since much larger numbers of corms are produced. Single clusters taken while the bulbs are being harvested, number as high as 37 corms of various sizes developed from medium sized stock planted the preceding August. Also the production of cormels in clusters in the leaf axils is very high in this new variety.

The features which I claim distinguish my new variety from all other known varieties of freesias are as follows:

First; Giant size of plant and flowers.

Second; My flowers have a more regular and more pleasing lily-like shape and form, both as to the six segments or lips of the perianth and as to the funnel portion of the perianth.

Third; Waxy, pure white appearance of flowers without the usual visible yellow lip.

Fourth; Brighter green foliage, long stems and strong, upright growth.

Fifth; Smaller size and greater number of corms, large number of cormlets, all of which gives rapid reproduction.

Sixth; Buds whiten early and flowers last long.

I claim:

The variety of freesia herein described and shown, characterized particularly by its large size, waxy white lily-like color, regular and pleasing shape, bright green foliage, and the relatively small size but great number of corms produced.

W. RUSSELL ELDER.